US011080852B2

(12) United States Patent
Liao et al.

(10) Patent No.: US 11,080,852 B2
(45) Date of Patent: Aug. 3, 2021

(54) METHOD AND SYSTEM OF ANALYZING MEDICAL IMAGES

(71) Applicant: Chang Gung Memorial Hospital, Linkou, Taoyuan (TW)

(72) Inventors: Chien-Hung Liao, Taoyuan (TW); Chi-Tung Cheng, Taoyuan (TW); Tsung-Ying Ho, Taoyuan (TW); Tao-Yi Lee, Taoyuan (TW); Ching-Cheng Chou, Taoyuan (TW)

(*) Notice: Subject to any disclaimer, the term of this patent is extended or adjusted under 35 U.S.C. 154(b) by 123 days.

(21) Appl. No.: 16/544,479

(22) Filed: Aug. 19, 2019

(65) Prior Publication Data
US 2020/0058123 A1 Feb. 20, 2020

Related U.S. Application Data

(60) Provisional application No. 62/719,664, filed on Aug. 19, 2018.

(51) Int. Cl.
*G06T 7/00* (2017.01)
*G16H 30/20* (2018.01)
*A61B 6/03* (2006.01)
*G06T 7/60* (2017.01)
*G06T 7/11* (2017.01)
*A61B 5/055* (2006.01)

(52) U.S. Cl.
CPC .......... *G06T 7/0012* (2013.01); *A61B 6/032* (2013.01); *G06T 7/60* (2013.01); *G16H 30/20* (2018.01); *A61B 5/055* (2013.01); *G06T 7/11* (2017.01); *G06T 2207/10116* (2013.01); *G06T 2207/20081* (2013.01); *G06T 2207/30008* (2013.01)

(58) Field of Classification Search
None
See application file for complete search history.

(56) References Cited

U.S. PATENT DOCUMENTS

2007/0274584 A1* 11/2007 Leow .................. G03B 42/02
                                                    382/132
2012/0143037 A1*  6/2012 Najarian ............... G06T 7/11
                                                    600/407
(Continued)

FOREIGN PATENT DOCUMENTS

CN     108305248 A     7/2018
CN     108309334 A     7/2018
WO     WO 2010/117575 A2  10/2010

OTHER PUBLICATIONS

Cheng, Chi-Tung et al: "Application of a deep learning algorithm for detection and visualization of hip fractures on plain pelvic radiographs", European Radiology, Springer International, Berlin, DE, Apr. 1, 2019 (Apr. 1, 2019), pp. 5469-5477, vol. 29, No. 10.

(Continued)

*Primary Examiner* — Fayyaz Alam
(74) *Attorney, Agent, or Firm* — Muncy, Geissler, Olds & Lowe, P.C.

(57) ABSTRACT

The present invention seeks to provide a method of analyzing medical image, the method comprises receiving a medical image; applying a model stored in a memory; analyzing the medical image based on the model; determining the medical image including a presence of fracture; and, transmitting an indication indicative of the determination.

14 Claims, 4 Drawing Sheets

(56) References Cited

U.S. PATENT DOCUMENTS

2014/0163375 A1* 6/2014 Wasielewski ........ A61B 8/4427
600/443
2016/0364631 A1 12/2016 Reicher et al.
2019/0336097 A1* 11/2019 Bregman-Amitai ... G06K 9/627

OTHER PUBLICATIONS

Gale, William et al: "Detecting hip fractures with radiologist-level performance using deep neural networks", arxiv.org, Cornell University Library, 201 Olin Library Cornell University Ithaca, NY 14853, Nov. 17, 2017.

Urakawa, Takaaki et al: "Detecting intertrochanteric hip fractures with orthopedist-level accuracy using a deep convolutional neural network", Skeletal Radiology, Springer, Berlin, DE, Jun. 28, 2018 (Jun. 28, 2018), pp. 239-244, vol. 48, No. 2.

Tomita, Naofumi et al: Deep neural networks for automatic osteoporotic vertebral fractures on CT scans Computers in Biology and Medicine, New York, NY, US, May 8, 2018 (May 8, 2018), pp. 8-15, vol. 98.

Bar, Amir et al: "Compression fractures detection on CT Progess in Biomedical optics and imaging SPIE"—International Society for Optical Engineering, Bellingham, WA, US, Mar. 3, 2017 (Mar. 3, 2017), pp. 1013440-1013440, vol. 10134.

Selvaraju, Ramprasaath R et al: "Grad-CAM: Visual Explanations from Deep Networks via Gradient-Based Localization" 2017 IEEE International Conference On Computer Vision IEEE, Mar. 21, 2017 (Mar. 21, 2017), pp. 618-626.

Mazurowski, Maciej A, et al: "Deep learning in radiology: an overview of the concepts and a survey of the state of the art" arxiv.org, Cornell University Library, 201, Olin Library Cornell University Ithaca, NY 14853, Feb. 10, 2018.

Umadevi, N. & Geethalakshmi, S. N., "Multiple classification system for fracture detection in human bone x-ray images." 2012 Third International Conference on Computing, Communication and Networking Technologies, Dec. 31, 2012, pp. 1-8.

* cited by examiner

METHOD AND SYSTEM OF ANALYZING MEDICAL IMAGES

CROSS-REFERENCE TO RELATED APPLICATION

This application claims the benefit of U.S. Application No. 62/719,664, filed on 19 Aug. 2018, the entire disclosure of which is incorporated herein by reference.

FIELD OF THE INVENTION

The present invention relates to analyzing images; particularly, the present invention relates to analyzing medical images.

BACKGROUND OF THE INVENTION

The number of hip fractures and the resulting post-surgical outcome are significant public health concerns worldwide. The number of hip fractures continues to increase due to prolonged human lifespan and the growing elderly populations. Approximately 20-30% of patients with a hip fracture encounter life-threatening situations within a year, and the majority of the patients experience significant functional loss. Because of the weight-bearing nature of the region, patients who have clinically 'silent' fractures rapidly develop severe pain and immobility. Early detection and surgery are critical for patient survival and the preservation of hip function. Postponed management of hip fractures results in a poor prognosis and even an increased risk of death years later. Therefore, detecting hip fractures as soon as possible is critical for remote mortality and medical outcomes.

Frontal pelvic radiographs (PXRs) are an essential and widely used tool for image evaluation for hip fractures. However, hip fracture assessment using frontal pelvic radiographs is not optimal. Studies show that mis-diagnosis by qualified medical professionals, are as high as 7-14%. The mis-diagnosis delays the proper diagnosis and treatments, and worsen prognosis of hip fracture. To avoid further health sequelae and medical costs associated with a delayed diagnosis, additional radiographs, nuclear medicine bone scans, computed tomography (CT) scans, and magnetic resonance imaging (MRI) scans have been recommended as routine diagnostics. However, it is not an effective, efficient or economical method to use these diagnostic tools as routine examinations.

Computerized analysis of medical image based on deep learning has shown potential benefits as a diagnostic strategy and has recently become feasible. The application of deep convolutional neural networks (DCNNs) for detecting hip fractures has not been evaluated completely.

There is a need to improve the accuracy of fracture diagnosis using medical images. The present invention addresses this need and other needs.

SUMMARY OF THE INVENTION

Accordingly, an improved method of analyzing the medical image is proposed by the present invention.

An embodiment of the present invention provides a method of analyzing a medical image, the method comprises receiving a medical image; applying a model stored in a memory; analyzing the medical image based on the model; determining the medical image including a presence of fracture; and, transmitting an indication indicative of the determination.

In one embodiment, applying the model comprises receiving training data from a dataset, the training data including a plurality of training images, each training image includes diagnosis data; developing the model using the training data; and storing the model in a memory.

In one embodiment, the method further comprises identifying a portion of each training image, wherein the portion includes the diagnosis data; and developing the model using the training data and the portion identified.

In one embodiment, the method of analyzing the medical image disclosed herein is based on a model comprises augmenting the medical image.

In one embodiment, augmenting the medical image comprises at least one of zooming of the medical image; flipping the medical image horizontally; flipping the medical image vertically; or rotating the medical image.

In one embodiment, developing the model comprises using machine learning technique or deep neural network learning technique.

In one embodiment, the method further comprises identifying a lesion site.

In one embodiment, the method further comprises generating a heatmap to identify the lesion site.

In one embodiment, the indication comprise a heatmap.

In one embodiment, the presence of fracture comprise fracture in a hip region.

An embodiment of the present invention provides a system of analyzing medical image, the system comprising a scanner for receiving a medical image; a processor being configured to: apply a model; analyze the medical image based on the model; and determine the medical image comprising a presence of fracture; and a display for displaying an indication indicative of the determination. In an exemplary embodiment, the medical image is a raw pixel image. In another exemplary embodiment, the medical image is not a cropped image.

In one embodiment, the processor is configured to apply the model comprising: receiving training data from a dataset, the training data including a plurality of training images, each training image includes diagnosis data; developing the model using the training data; and storing the model in the memory.

In one embodiment, the processor is configured to retrieve the model further comprising identifying a portion of each training image; and developing the model using the training data and the portion identified.

In one embodiment, the processor is configured to analyze the medical image based on the model comprising augmenting the medical image.

In one embodiment, augmenting the medical image comprising at least one of zooming of the medical image; flipping the medical image horizontally; flipping the medical image vertically; and, rotating the medical image.

In one embodiment, developing the model comprising using machine learning technique or deep neural network learning technique.

In one embodiment, the processor is further configured to identify a lesion site.

In one embodiment, the processor is further configured to generate a heatmap to identify the lesion site.

In one embodiment, the indication is a heatmap.

In one embodiment, the fracture is a fracture in the hip or pelvic region and the medical image is frontal pelvic radiograph (PXR).

An embodiment of the present invention provides a model for automatically analyzing pelvic radiographs using image analytics developed using previously-analyzed transfer learning process of radiographs, the model comprising: receive training information from the established dataset, the training information including a plurality of radiographs with normal and abnormal diagnosis; determine a portion of each of the plurality of radiographs including diagnostic information, perform deep neural network learning to develop a model using the training information and the portion determined for each of the plurality of radiographs, portion determined for presence of fracture or not of radiographs, application of the heatmap to localize the pathologic site.

The present invention is defined by the following claims, and nothing in this section should be taken as a limitation on those claims. Further aspects and advantages of the invention are discussed below in conjunction with the preferred embodiments and may be later claimed independently or in combination.

DETAILED DESCRIPTION OF THE INVENTION

Figure 1:
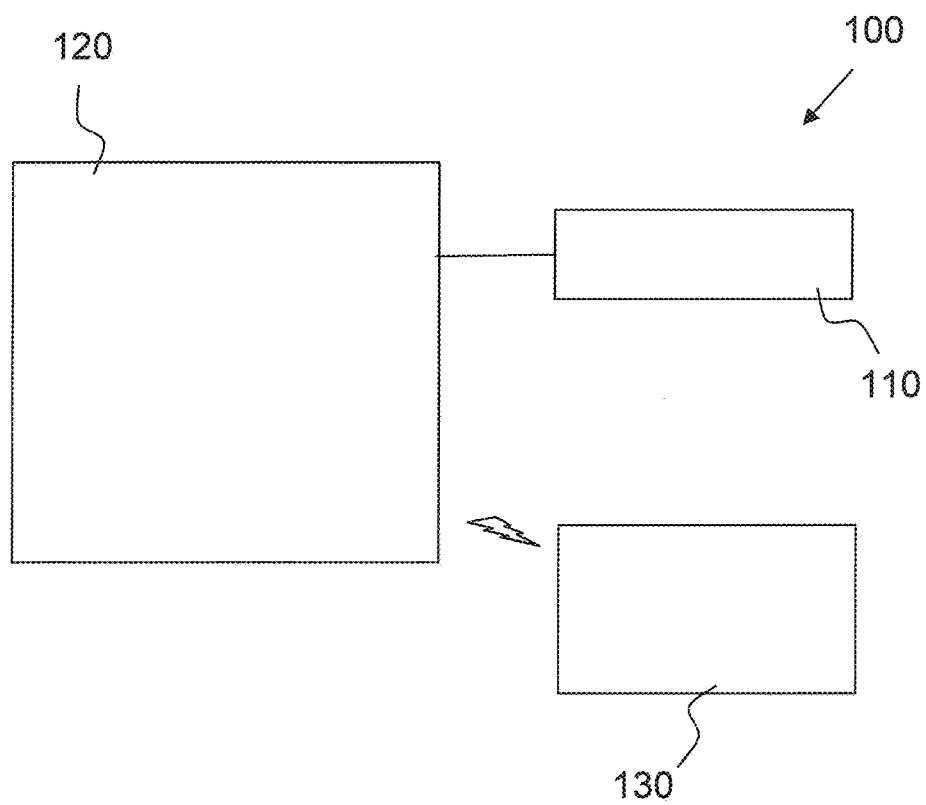
FIG. 1 is a schematic diagram of an embodiment of a system of analyzing medical image.

An embodiment of the present invention is described with reference to FIG. 1.

A system 100 of analyzing medical image is provided. The system 100 comprises a scanner 110 for receiving a medical image. The scanner may be an X-ray (radiograph), Magnetic resonance imaging (MRI) or a computed tomography (CT) scanner. The medical image may be X-ray, CT or MRI image of a region of a subject (such as an upper/lower body of a subject) or a specific-site of a subject. The system further comprises a processor 120 for (a) analyzing the medical image, (b) determining if the medical image includes a presence of fracture and (c) transmitting an indication based on the determination in step (b) to a display 130 for visually presenting the indication. The processor may be a microprocessor or a processing unit, such as a field-programmable gate array (FPGA) or other suitable programmable processing unit. The display 130 may be a screen of a computer or a smartphone, a light emitting diode (LED) light indicator or any other suitable display capable of visually presenting the indication.

Figure 2:
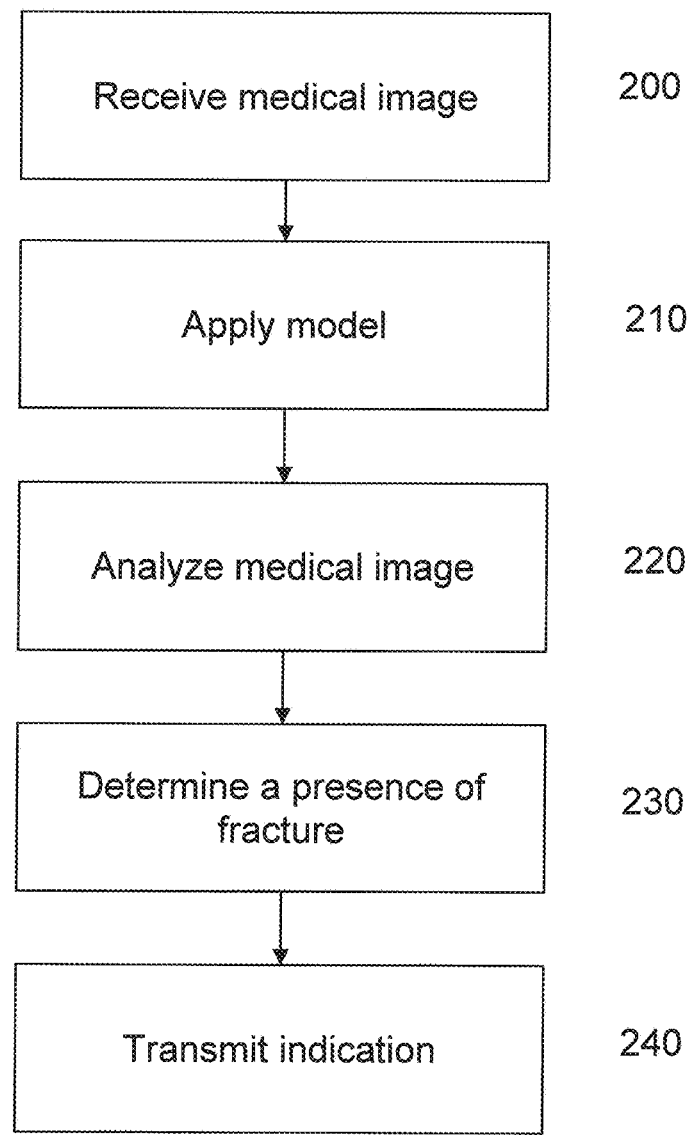
FIG. 2 is a flow chart of an embodiment of a method of analyzing medical image.

Referring to FIG. 2, when in operation, the processor 120 receives a medical image at step 200. The medical image can be a radiograph such as an X-ray, MRI or a CT scan. At step 210, the processor 120 applies a model stored in a memory. The memory can be a storage of the processor 120 or a storage external to and in communication with the system 100. The model may be an iteratively learning model, or a model generated from pre-training processes. The system analyzes the medical image based on the model at step 220 and determines if the medical image includes a presence of fracture at step 230. At step 240, the processor 120 transmits an indication indicative of the determination.

Advantageous, the present invention provides the method of analyzing the medical image with the processor by applying the model. This allows the medical image to be more rapidly and accurately analyzed. In an exemplary embodiment, the image is 500×500 pixels to 3000×3000 pixels, less than or about 3000×3000 pixels, less than or about 2000×2000 pixels, less than or about 1500×1500 pixels, less than or about 1200×1200 pixels, less than or about 1000×1000 pixels, less than or about 900×900 pixels, less than or about 800×800 pixels, less than or about 700×700 pixels, less than or about 600×600 pixels or less than or about 512×512 pixels.

In one embodiment, applying the model comprises receiving training data from a dataset, the training data including a plurality of training images, each training image includes diagnosis data; developing the model using the training data; and storing the model in the memory. This allows the model to be developed and the analysis to be more accurate based on the model. The model may be regularly updated with further datasets.

In one embodiment, identifying a portion of each training image, wherein the portion includes the diagnosis data; and developing the model using the training data and the portion identified. The portion may be a suspected lesion site.

In one embodiment, analyzing the medical image based on the model comprising augmenting the medical image. This allows the medical image to be clearer or allows analyzing to be more easily and/or effectively. Augmenting the medical image may comprise at least one of zooming of the medical image, flipping the medical image horizontally, flipping the medical image vertically, and rotating the medical image.

In one embodiment, developing the model comprising using machine learning technique or deep neural network learning technique. This allows the model to be efficiently developed, and the model may be easily optimized using different techniques. It should be appreciated that any machine learning techniques can be used with appropriate computer hardware.

In one embodiment, the method further comprises identifying a lesion site. This allows the identification of the lesion site to be more efficient. Advantageously, this allows the medical practitioner to categorize the potential issue or pathology. The method may further comprise generating a heatmap to identify the lesion site to thereby provide a clear map of the potential issues.

In one embodiment, the indication comprises a heatmap. This allows the potential issues to be easily displayed with a clear map of the probabilities.

In one embodiment, the presence of fracture comprises fracture in a hip region. A specific embodiment of the present invention for analyzing hip fractures in frontal pelvic radiograph (PXR) using deep learning algorithm is hereafter described.

In this embodiment, a fracture diagnosis algorithm is trained based on the DCNN to examine PXRs and investigated the performance compared with a qualified medical professional. It is also investigated that the validity of this algorithm by lesion visualization using Grad-CAM.

Demographic data, medical data, perioperative procedures, hospital procedures, medical imaging findings, follow-up data and information regarding complications were recorded prospectively in a computerized database.

Hospital inpatients with a PXR performed on the date of injury were identified in the Year 2012-2016 Trauma Registry as the PXR dataset. The PXRs were stored automatically with a Python script for a picture archiving and communication system (PACS) viewer. The size of stored images varies from 2,128×2,248 pixels to 2,688×2,688 pixels, and the color is 8-bit grayscale.

Another hundred patients who had PXRs performed were identified from the Year 2017 Trauma Registryas the Validation Set. There were 25 patients with femoral neck fractures, 25 with intertrochanteric fractures and 50 without hip fractures. The PXRs performed on the date of injury were prepared as an independent testing dataset.

After the PXR datasets were established, the images were initially labeled as a hip fracture or no hip fracture according to the diagnosis in the trauma registry. The radiologist's report, diagnosis, clinical course and other related images, such as CT or other views of the hip joint, were reviewed if the label was questionable.

DCNNs are used in computer vision and medical image recognition. The basic concept is to use pixel values from a digital image as inputs using techniques, such as convolution and pooling, on each layer and to adjust the weights in the neural network according to the difference between the output and true label. After a significant amount of imaging input is used as the training material, the weights in the neural network are adjusted to fit the problem. DenseNet-121 as the structure of neural network is used. The structure contains a dense block with a skip connection designed within the dense block. The input images were resized to 512×512 pixels with an 8-bit grayscale color to reduce the complexity and computation. Most studies use ImageNet as a pre-training material for "transfer learning". The limb dataset as the pre-training material is used in this example. The model was initially trained to identify the body part in view on each limb radiograph. 90% of the limb dataset is randomly selected for training and 10% for validation. The pre-trained weights of the DCNN were preserved for PXR training. The PXR dataset was separated as 80% for training and 20% for validation. During the training process, image augmentation was applied with a zoom of 10% (range from 1-25% or 5-20%), horizontal flip, vertical flip, and rotation of 10 degrees (range from 1 to 30 degrees or 5 to 25 degrees). The batch size was 8, and the Adam optimizer was used. The initial learning rate was 10-3 with a reduced learning rate on the plateau. The final model was trained with 60 epochs under the above hyperparameters.

The trained hip model was tested with the Validation Set to evaluate its accuracy for identifying hip fractures. The probability generated by the model of hip fracture was evaluated with a receiver operating characteristic (ROC) curve and the area under the curve (AUC). A confusion matrix was also calculated using a cut-off level of probability 0.5 of hip fracture. For those PXRs model predicts fracture, it is also used a Grad-CAM to generate a heatmap that the model activated for the hip fracture to provide evidence that the model indeed recognized the fracture site. The heatmaps were also reviewed by a radiologist to compare with the fracture site on the original image to evaluate the ability of localization. Experts from the surgical, orthopedics, emergency and radiology departments were recruited to evaluate the accuracy of each subspecialist in interpreting the PXRs.

The software used to build the DCNN was based on an Ubuntu 14.04 operating system with TensorFlow 1.5.1 and Keras 2.1.4 open-source library with Python 3.6.5 (Python Software Foundation). The training process was run on an Intel® Core™ i7-7740X CPU 4.30 GHz with GeForce® GTX 1080 Ti GPU. All statistical analyses were performed using R 3.4.3 with extension packages "pROC", "epiR", "Publish" and "ggplot2". Continuous variables were evaluated with Student's t-test, and categorical variables were evaluated with the chi-square test. Comparison is made between the hip model and specialists using the sensitivity, specificity, false-negative rate and false-positive rate, and the F1 scores and 95% confidence intervals (CIs) were calculated. ROC curves and AUCs were used to evaluate the performance of the model.

3605 PXRs are obtained to build the model.

After applying the hip model to one of PXR dataset, the accuracy, sensitivity, specificity, false-negative rate and F1 score of the model were 91% (n=100; 95% CI, 84%-96%), 98% (95% CI, 89%-100%), 84% (95% CI, 71%-93%), 2% (95% CI, 0.3%-17%) and 0.916 (95% CI, 0.845-0.956), respectively. A total of 21 medical professionals completed the questionnaire. The range of sensitivity of primary physicians (except radiologists and orthopedic surgeons) was 84% to 100% (mean, 95.6%; 95% CI, 93.6%-97.6%), and the specificity ranged from 46% to 94% (mean, 82.2%; 95% CI, 76.2%-88.3%). The experts, including two radiologists and four orthopedic surgeons, completed the questionnaire and achieved a mean sensitivity of 99.3% (95% CI, 98.2%-100%) and a specificity of 87.7% (95% CI, 81.5%-93.8%). The model achieved an AUC of 0.98 (95% CI, 0.96-1.00).

Figure 3:
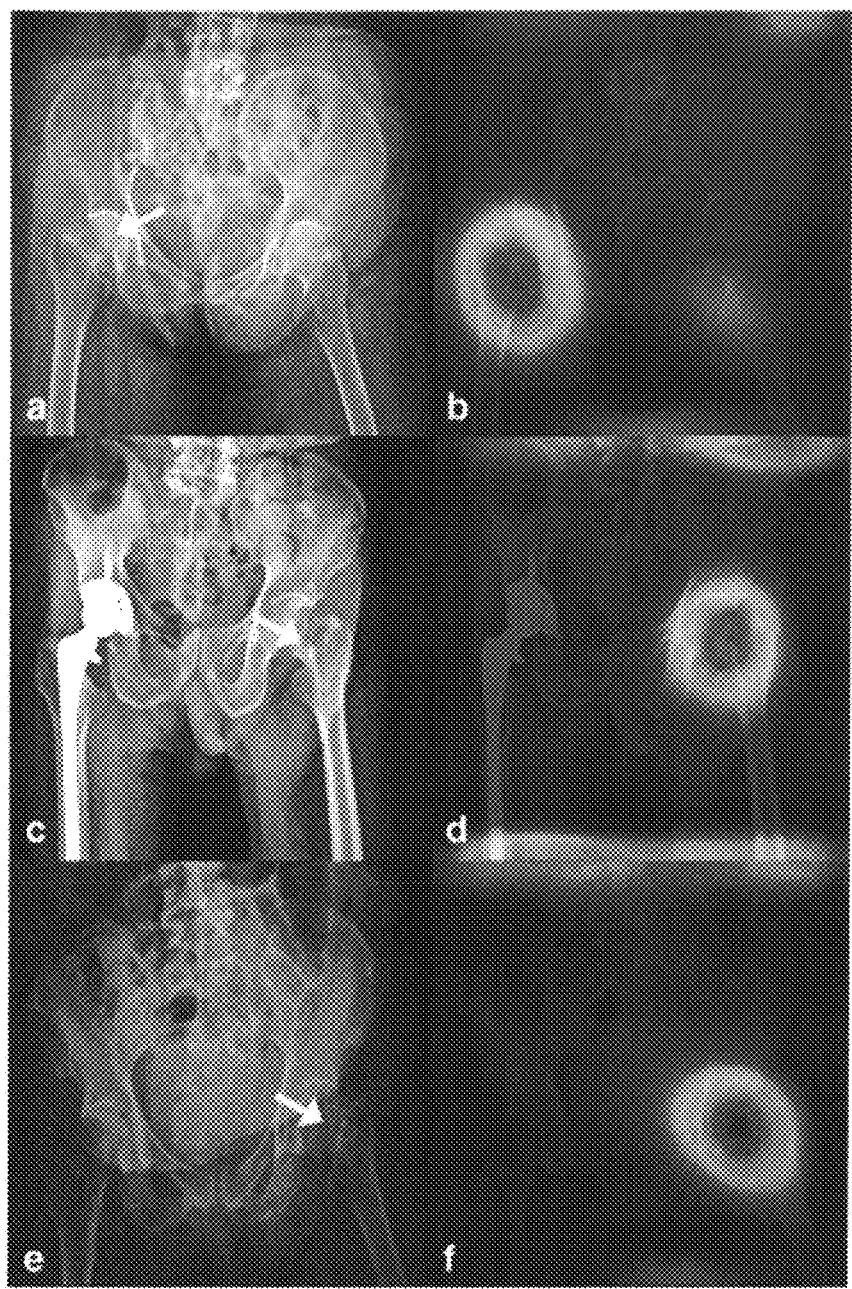
FIG. 3 is an assembly of images wherein images a, c and e are original pelvic radiographs with arrows indicating the fracture; and images b, d and f are Grad-CAM images generated according to an embodiment of the present invention corresponding to images a, c and e, respectively.
Figure 4:
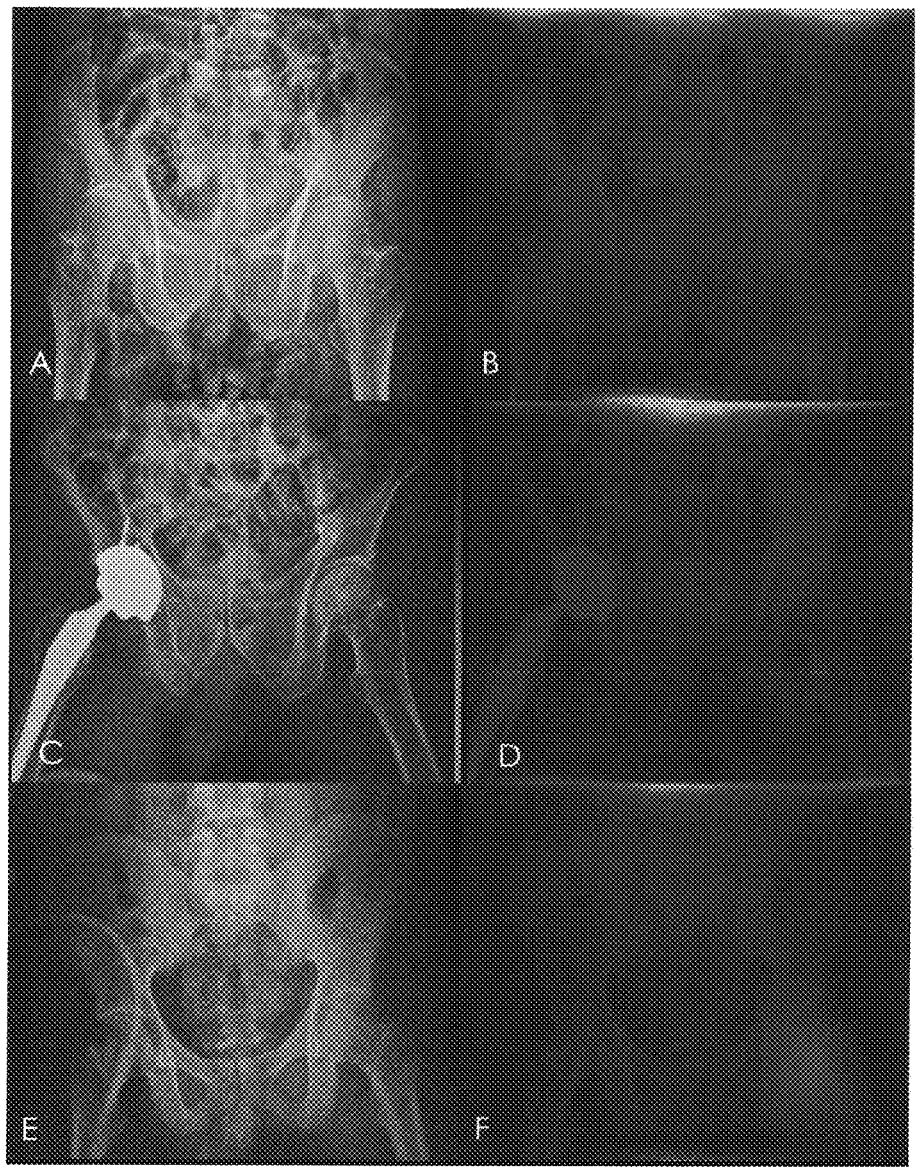
FIG. 4 is an assembly of images wherein images A, C and E are original pelvic radiographs; and images B, D and F are Grad-CAM images generated according to an embodiment of the present invention corresponding to images A, C and E, respectively.

After analyzing heatmap images, the model predicted the presence as well as the absence of hip fracture. Only two images identified the wrong activation site, and 95.9% of the activation area was located at the hip fracture site, as shown in FIG. 3. The model did not identify hip fracture site in normal PXRs, as shown in FIG. 4 with absence of heatmap images.

These results indicate that a DCNN can be trained to identify hip fractures within image datasets with high sensitivity (98%) and accuracy (91%).

The detection and diagnosis of hip fractures on PXRs could be performed by input a whole scale radiograph to a DCNN without identify specific region first. The deep learning algorithm also achieved an accuracy level that is compatible with the accuracy of radiologists and orthopedic surgeons.

The process of the present invention does not require extensive processing, lesion segmentation or extraction of domain-specific visual features. The system of the present invention requires limited handcrafted features, and it is trained end-to-end directly from image labels and raw pixels.

One paradox in DCNNs for analyzing medical images is the "black box" mechanism. Most deep learning works evaluating medical images use cropped images to avoid "black box" mechanisms and enhance the accuracy of final validation. Once the target is cropped to include the necessary features for recognition, the DCNN will detect the lesion more easily and quickly. In this study, instead of cropping images, the whole raw image matrix size was reduced to 512×512 pixels.

Inputting the whole PXR images is preferred because this method is integrated into the clinical pathway, more instinctual and physicians are more familiar with it. The dimensionality reduction also decreases the computational requirement and shortens the training time with an acceptable result. Furthermore, based on the model, this algorithm is applied to other types of fracture in PXRs.

The invention claimed is:

1. A method of analyzing a medical image, wherein the medical image is a whole scale radiograph, the method comprising:
   receiving the whole scale radiograph;
   applying a model stored in a memory;
   analyzing the whole scale radiograph based on the model without identifying the femoral neck in the whole scale radiograph;
   determining the whole scale radiograph including a presence of fracture; and,
   transmitting an indication indicative of the determination;
   wherein applying the model comprising:
   receiving training data from a dataset, the training data including a plurality of training images, each training image includes diagnosis data;
   developing the model using the training data; and
   storing the model in the memory, and
   wherein analyzing the whole scale radiograph based on the model comprising augmenting the whole scale radiograph, said augmenting is at least one of:
   zooming of the whole scale radiograph;
   flipping the whole scale radiograph horizontally;
   flipping the whole scale radiograph vertically; and
   rotating the whole scale radiograph.

2. The method of claim 1, wherein applying the model further comprising:
   identifying a portion of each training image, wherein the portion includes the diagnosis data; and
   developing the model using the training data and the portion identified.

3. The method of claim 1, wherein developing the model comprising using machine learning technique or deep neural network learning technique.

4. The method of claim 1, further comprising identifying a lesion site.

5. The method of claim 4, further comprising generating a heatmap to identify the lesion site.

6. The method of claim 1, wherein the presence of fracture comprises fracture in a hip or pelvic region.

7. The method of claim 1, wherein the whole scale radiograph is a frontal pelvic radiograph and 500×500 pixels to 3000×3000 pixels.

8. A system of analyzing a medical image, wherein the medical image is a whole scale radiograph, the system comprising:
   a scanner for receiving the whole scale radiograph;
   a processor being configured to:
   apply a model;
   analyze the whole scale radiograph based on the model without identifying the femoral neck in the whole scale radiograph; and
   determine the whole scale radiograph comprising a presence of fracture; and
   a display for displaying an indication indicative of the determination;
   wherein the processor is configured to apply the model comprising
   receiving training data from a dataset, the training data including a plurality of training images, each training image includes diagnosis data;
   developing the model using the training data; and
   storing the model in the memory, and
   wherein the processor is configured to analyze the whole scale radiograph based on the model comprising augmenting the whole scale radiograph, said augmenting is at least one of:
   zooming of the whole scale radiograph;
   flipping the whole scale radiograph horizontally;
   flipping the whole scale radiograph vertically; and,
   rotating the whole scale radiograph.

9. The system of claim 8, wherein the processor is configured to retrieve the model further comprising:
   identifying a portion of each training image; and
   developing the model using the training data and the portion identified.

10. The system of claim 8, wherein developing the model comprising using machine learning technique or deep neural network learning technique.

11. The system of claim 8, wherein the processor is further configured to identify a lesion site.

12. The system of claim 11, wherein the processor is further configured to generate a heatmap to identify the lesion site.

13. The system of claim 8, wherein the presence of fracture comprise fracture in a hip or pelvic region.

14. The system of claim 13, wherein the whole scale radiograph is a frontal pelvic radiograph and 500×500 pixels to 3000×3000 pixels.

* * * * *